(12) United States Patent
Burnam

(10) Patent No.: US 11,116,734 B2
(45) Date of Patent: *Sep. 14, 2021

(54) PETROLATUM-BASED COMPOSITIONS AND METHODS OF TREATMENT FOR ONYCHOMYCOSIS

(71) Applicant: GLOBAL HEALTH SOLUTIONS LLC, Rome, GA (US)

(72) Inventor: Bradley Burnam, Calabasas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/745,308

(22) Filed: Jan. 16, 2020

(65) Prior Publication Data

US 2020/0147009 A1 May 14, 2020

Related U.S. Application Data

(63) Continuation-in-part of application No. 15/167,099, filed on May 27, 2016, now Pat. No. 10,722,461.

(60) Provisional application No. 62/182,034, filed on Jun. 19, 2015, provisional application No. 62/319,449, filed on Apr. 7, 2016, provisional application No. 62/326,150, filed on Apr. 22, 2016, provisional application No. 62/338,995, filed on May 19, 2016, provisional application No. 62/793,317, filed on Jan. 16, 2019.

(51) Int. Cl.
| | | |
|---|---|---|
| *A61K 31/14* | (2006.01) | |
| *A61K 47/06* | (2006.01) | |
| *A61K 45/06* | (2006.01) | |
| *A61P 31/10* | (2006.01) | |
| *A61K 31/4412* | (2006.01) | |
| *A61K 31/4164* | (2006.01) | |
| *A61K 31/135* | (2006.01) | |

(52) U.S. Cl.
CPC ............ *A61K 31/14* (2013.01); *A61K 31/135* (2013.01); *A61K 31/4164* (2013.01); *A61K 31/4412* (2013.01); *A61K 45/06* (2013.01); *A61K 47/06* (2013.01); *A61P 31/10* (2018.01)

(58) Field of Classification Search
None
See application file for complete search history.

(56) References Cited

U.S. PATENT DOCUMENTS

2009/0269394 A1* 10/2009 Baker, Jr. ............. A61K 47/186
424/447
2017/0232004 A1* 8/2017 Genberg ............. A61K 31/575
514/3.4

* cited by examiner

*Primary Examiner* — David J Blanchard
*Assistant Examiner* — Sarah J Chickos
(74) *Attorney, Agent, or Firm* — Polsinelli PC

(57) ABSTRACT

Compositions and methods for the treatment of onychomycosis. The compositions include a pharmaceutically effective amount of one or more anti-fungal agents in a petrolatum carrier. The one or more anti-fungal agents may include, for example, terbinafine HCl, ciclopirox, ciclopirox olamine, fluconazole, itraconazole, ketoconazole, amorolfine, efinaconazole, clotrimazole, miconazole (miconazole nitrate), and any combination thereof.

19 Claims, 2 Drawing Sheets

PETROLATUM-BASED COMPOSITIONS AND METHODS OF TREATMENT FOR ONYCHOMYCOSIS

CROSS-REFERENCE TO RELATED APPLICATIONS

This application is a continuation-in-part of U.S. patent application Ser. No. 15/167,099, filed May 27, 2016, which claims priority to U.S. Provisional Application No. 62/182,034, filed Jun. 19, 2015, U.S. Provisional Application No. 62/319,449, filed Apr. 7, 2016, U.S. Provisional Application No. 62/326,150, filed Apr. 22, 2016, and U.S. Provisional Application No. 62/338,995, filed May 19, 2016. This application also claims the benefit of U.S. Provisional Application Ser. No. 62/793,317, entitled "Petrolatum-Based Compositions and Methods of Treatment for Onychomycosis," filed Jan. 16, 2019. The contents of each of the aforementioned patent applications are incorporated by reference herein, for all purposes, in their entirety.

FIELD

The present disclosure is broadly concerned with petrolatum-based compositions for the treatment and prevention of onychomycosis. The disclosure is also concerned with methods for the treatment of onychomycosis using petrolatum-based compositions.

BACKGROUND

Onychomycosis, also known as tinea unguium, is a highly prevalent fungal infection of the nail affecting 35 million people in the United States. Without treatment, onychomycosis may damage the nail unit and spread to other fingers or toes and skin. Onychomycosis affects 1 in 3 diabetics and increases the risk of secondary infections which may lead to foot disorders and limb amputations. Since, onychomycosis is generally a non-life threatening infection, it should ideally be treated topically. However, current topical treatments do not penetrate the nail plate rendering them ineffective due to an inability to reach microbes below the nail plate. The use of oral medications for onychomycosis are limited by safety concerns including liver toxicity, drug-drug interactions, loss of taste, and migraine headaches. As a result, 85% of the 1 in 10 Americans affected by onychomycosis fail to seek treatment due to limited safe and effective treatment options. Accordingly, additional compositions and methods for the treatment of onychomycosis are desirable.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION

Figure 1:
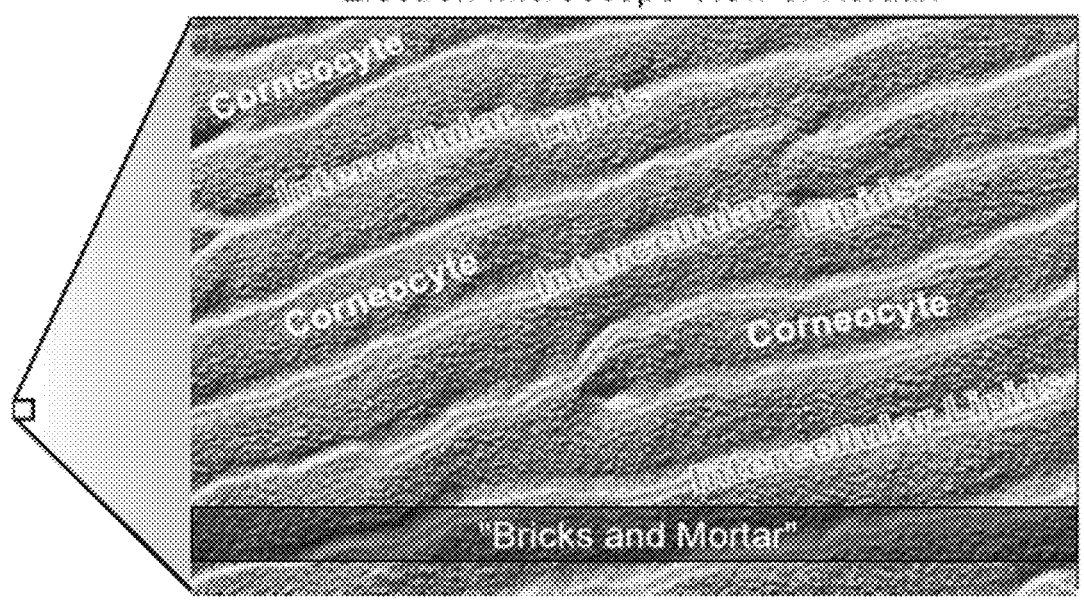
FIG. 1 depicts an electron microscope micrograph showing the structure of typical nails, according to an exemplary embodiment of the present disclosure.
Figure 2:
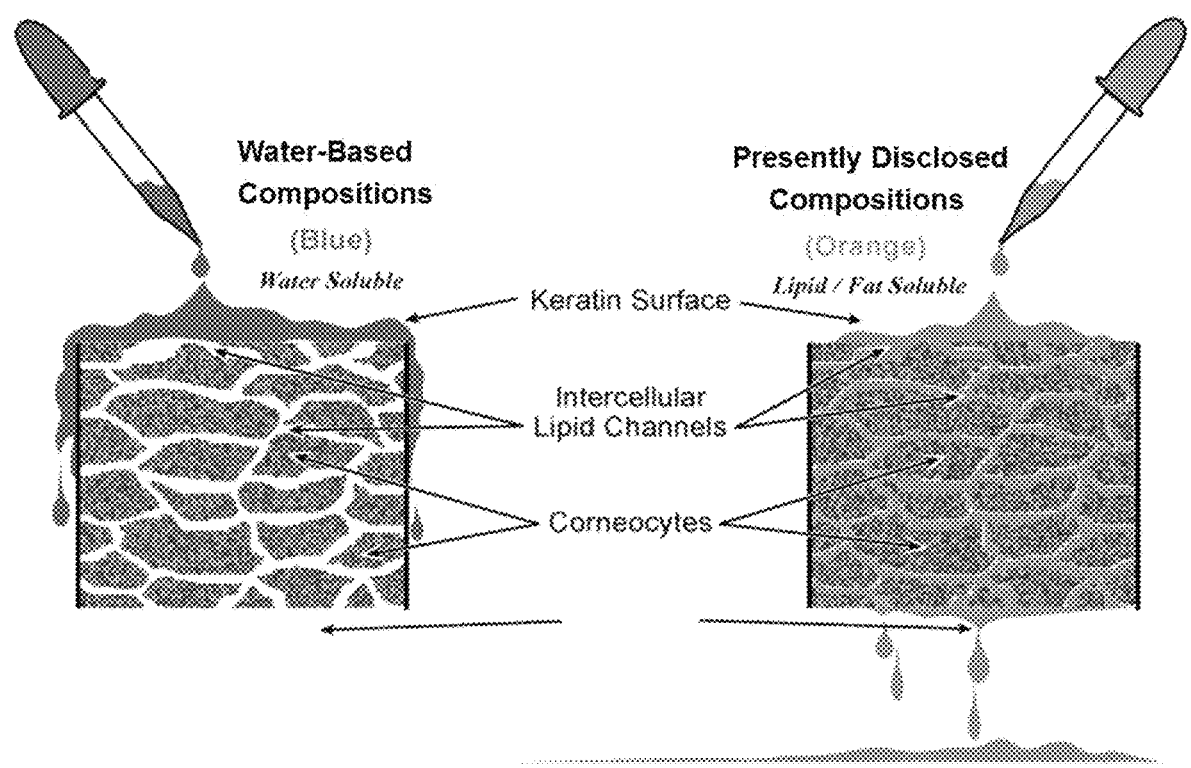
FIG. 2 is a diagrammatic view depicting penetration of the presently disclosed topical compositions through the nail to deliver one or more anti-fungal agents to the site of infection below the nail, according to an exemplary embodiment of the present disclosure.

The present disclosure provides compositions and methods for the treatment of onychomycosis. It has been unexpectedly discovered that the presently disclosed compositions comprising one or more anti-fungal agents dispersed as nanodroplets in a petrolatum carrier are effective in the treatment of onychomycosis. In particular, it has been unexpectedly discovered that the presently disclosed compositions are capable of penetrating the keratin surface and nail plate to deliver a pharmaceutically effective amount of anti-fungal agent directly to the site of infection. In particular, as depicted in FIG. 1, the presently disclosed compositions are capable of penetrating the keratin surface of the nail to carry active ingredients, such as anti-fungal agents, through the channels of the lipid bilayers and deliver the active ingredients to the nail bed and throughout the nail itself. FIG. 1 depicts an electron micrograph of skin or nail comprising corneocytes interspaced by intercellular lipid bilayers. As shown in FIG. 2, water-based topical formulations cannot penetrate the corneocytes nor pass through the intercellular lipids interspersed between the corneocytes. However, the presently disclosed petrolatum-based compositions are capable of passing through the intercellular lipid channels to penetrate the epidermal layer and enable deep delivery of antifungal ingredients, such as one or more anti-fungal agents, to the site of the infection below the nail.

According to at least one aspect of the present disclosure, a method of treating onychomycosis in a subject is provided. The method may include applying a petrolatum-based composition to the nail of a subject in need of treatment. The petrolatum-based composition may include a pharmaceutically effective amount of one or more anti-fungal agents in a petrolatum carrier. In at least some instances, the one or more anti-fungal agents is dispersed in the petrolatum carrier to form a stable petrolatum-based suspension. In some cases, the one or more anti-fungal agents is dispersed in the petrolatum carrier in the form of nanodroplets. The nanodroplets may comprise, for example, one or more fungal agents and a polar solvent. For instance, the one or more anti-fungal agents may be dissolved in a polar solvent to form an anti-fungal agent solution and the anti-fungal agent solution dispersed in the petrolatum to form a stable suspension. The one or more anti-fungal agents may include, for example, terbinafine HCl, ciclopirox, ciclopirox olamine, fluconazole, itraconazole, ketoconazole, amorolfine, efinaconazole, clotrimazole, miconazole (miconazole nitrate), and any combination thereof.

In at least some instances, the onychomycosis may be distal subungual onychomycosis, or white superficial onychomycosis (WSO), or proximal subungual onychomycosis, or Candidal onychomycosis. In some cases, the onychomycosis may be caused by *Trichophyton rubrum* (*T. rubrum*), or caused by *Candida*, or caused by *Candida auris* (*C. auris*). In at least some instances, the onychomycosis may be caused by multi-drug resistant *C. auris*.

The presently disclosed petrolatum-based composition may include, for example, greater than about 80% by weight petrolatum, or greater than about 90% by weight petrolatum, or greater than about 95% by weight petrolatum. The petrolatum-based composition may include from about 0.05% to about 5% by weight of the one or more anti-fungal agents, or from about 0.05% to about 3% by weight of the one or more anti-fungal agents, or from about 0.1% to about 1% by weight of the one or more anti-fungal agents, or from about 0.2% to about 0.6% by weight of the one or more anti-fungal agents, or from about 0.3% to about 0.5% by weight of the one or more anti-fungal agents, or from about 0.1% to about 3.5% by weight of the one or more anti-fungal agents, or from about 0.05% to about 2.5% by weight of the one or more anti-fungal agents, or from about 0.5% to about 3% by weight of the one or more anti-fungal agents, or from about 0.5% to about 2.5% by weight of the one or more anti-fungal agents, or from about 1.5% to about 2.5% by weight of the one or more anti-fungal agents. In at least some instances, the petrolatum-based composition contains no emulsifier. In other instances, the petrolatum-based composition excludes an added emulsifier. As used herein, the term "added emulsifier" refers to an emulsifier in addition to the presently claimed components of the petrolatum-based composition.

In at least some instances, the petrolatum-based composition may further include a cationic biocide selected from the group consisting of benzalkonium chloride, cetrimide, chlorhexidine, and any combination thereof. In some instances, the petrolatum-based composition may include from about 0.001% to about 0.15% by weight benzalkonium chloride (BZK), or from about 0.001% to about 0.01% by weight BZK, or from about 0.005% to about 0.007% by weight BZK. In at least some instances, the presently disclosed petrolatum-based compositions may be prepared by a process that includes: (a) dissolving the one or more anti-fungal agents in a polar solvent to give a anti-fungal agent solution; (b) heating the petrolatum to a temperature sufficient to cause the petrolatum to melt to give a melted petrolatum and heating the anti-fungal agent solution to a temperature higher than the temperature of the melted petrolatum to give a heated anti-fungal agent solution; (c) mixing the melted petrolatum and the heated anti-fungal agent solution to give a melted mixture; and (d) cooling the melted mixture to give the petrolatum-based composition. In some instances, the heated anti-fungal agent solution may have a temperature that is about 1° C. to about 5° C. higher than the temperature of the melted petrolatum. In some instances, the one or more anti-fungal agents are dissolved in a polar solvent to form an anti-fungal agent solution and the anti-fungal agent solution is dispersed in the petrolatum to form a stable suspension.

In at least some instances, the petrolatum-based compositions may include from about 0.01% to about 5% by weight terbinafine HCl, or from about 0.01% to about 5% by weight ciclopirox, or from about 0.01% to about 5% by weight ciclopirox olamine, or from about 0.01% to about 5% by weight fluconazole, or from about 0.01% to about 5% by weight itraconazole, or from about 0.01% to about 5% by weight ketoconazole, or from about 0.01% to about 5% by weight amorolfine, or from about 0.01% to about 5% by weight efinaconazole, or from about 0.01% to about 5% by weight clotrimazole, or from about 0.01% to about 5% by weight miconazole (miconazole nitrate), or any combination thereof.

According to at least one aspect of the present disclosure, the petrolatum-based composition may be a petrolatum-based composition that includes petrolatum and a pharmaceutically effective amount of one or more anti-fungal agents. In such cases, the compositions may include, for example, greater than about 80% by weight petrolatum. The compositions may also include a polar solvent. In some instances, the polar solvent may be water. In certain cases, the one or more anti-fungal agents and the polar solvent may be dispersed in the petrolatum in the form of nanodroplets. According to at least one aspect, the petrolatum-based compositions contain no emulsifier. In some instances, the one or more anti-fungal agents may be dissolved in a polar solvent to form an anti-fungal agent solution and the anti-fungal agent solution dispersed in the petrolatum. In such cases, the anti-fungal agent solution may be dispersed in the petrolatum to form a stable suspension such that the anti-fungal agent solution does not separate from the petrolatum for at least six months. According to at least one aspect of the present disclosure, the resultant petrolatum-based compositions do not require an emulsifier to form a stable suspension of one or more anti-fungal agents dispersed in the petrolatum. Further, the petrolatum-based compositions prepared according to this process does not require high shear mixing to form a stable suspension of one or more anti-fungal agents in petrolatum in the absence of an added emulsifier.

I. Compositions

According to one aspect, the present disclosure provides for compositions that are petrolatum-based. A petrolatum-based composition is made up primarily of petrolatum. The characteristics of a petrolatum-based composition differ from a composition containing only a small amount of petrolatum. In some embodiments, the petrolatum-based composition is greater than about 80% petrolatum. In other embodiments, the petrolatum-based composition is greater than about 81% petrolatum, greater than about 82% petrolatum, greater than about 83% petrolatum, greater than about 84% petrolatum, greater than about 85% petrolatum, greater than about 86% petrolatum, greater than about 87% petrolatum, greater than about 88% petrolatum, greater than about 89% petrolatum, greater than about 90% petrolatum, greater than about 91% petrolatum, greater than about 92% petrolatum, greater than about 93% petrolatum, greater than about 94% petrolatum, greater than about 95% petrolatum, greater than about 96% petrolatum, greater than about 97% petrolatum, greater than about 98% petrolatum, or greater than about 99% petrolatum. The petrolatum is preferably medical grade petrolatum.

The composition also contains one or more anti-fungal agents dispersed throughout the petrolatum. The one or more anti-fungal agents are the composition ingredient active in treating onychomycosis. In addition to the one or more anti-fungal agents, the presently disclosed compositions may also include cationic biocides, such as quaternary ammonium compounds, bisbiguanides, and polymeric biguanides. In particular, other cationic biocides that may be included in the compositions may include, but are not limited to, benzalkonium chloride, cetrimide, chlorhexidine, polihexanide biguanide (polihexanide, polyhexamethylene guanide, poly(iminoimidocarbonyl-iminoimidocarbonyl-iminohexamethylene), poly(hexamethylenebiguanide), polyaminopropyl biguanide) and salts or combinations thereof. In some instances, the presently disclosed compositions contain benzalkonium chloride (BZK) as a preservative. The total amount of cationic biocide in the composition generally constitutes less than about 1% by weight of the total composition. In preferred embodiments, the cationic biocide constitutes from about 0.1% to about 0.5% by weight, or more preferably, from about 0.1% to about 0.3% by weight to the total composition.

The remaining weight of the composition, typically from about 0.1% to about 6% by weight of the petrolatum-based composition, is liquid. In some instances, the composition contains about 5% water.

The one or more anti-fungal agents and cationic biocides that may be used in the presently disclosed compositions do not react with the petrolatum. Instead, the one or more anti-fungal agents and optional cationic biocides that may be included in the compositions are dispersed in the petrolatum as nanodroplets, and the petrolatum serves as a suspension matrix for the one or more anti-fungal agents and cationic biocides. "Nanodroplet," as used herein, is an aggregation of one or more anti-fungal agents and optionally any cationic biocide molecules in the petrolatum base. The nanodroplets typically contain a small amount of water or other polar solvent in addition to the one or more anti-fungal agents and optional cationic biocides. Nanodroplets in accordance with the present disclosure may vary in size but generally the longest dimension of the nanodroplets measures from about 10 nm to about 10,000 nm. In various embodiments, the nanodroplets range from about 10 nm to about 100 nm, from about 100 nm to about 1000 nm, from about 1000 nm to about 2000 nm, from about 2000 nm to about 3000 nm, from about 3000 nm to about 4000 nm, from about 4000 nm to about 5000 nm, from about 5000 nm to about 6000 nm, from about 6000 nm to about 7000 nm, from about 7000 nm to about 8000 nm, from about 8000 nm to about 9000 nm, from about 9000 nm to about 10,000 nm. The nanodroplets are dispersed through the petrolatum homogeneously.

Surprisingly, embodiments of the present invention do not require an emulsifier. An emulsifier, as used herein, is an added formulation ingredient used to reduce the tension between hydrophilic and hydrophobic surface ingredients, thereby facilitating the mixture hydrophilic and hydrophobic ingredients. Prior to the present invention, those skilled in the art expected that an emulsifier would be needed to disperse polar ingredients, such as a polar solvent, one or more anti-fungal agents, and cationic biocides, in a non-polar petrolatum suspension matrix. Where an emulsifier is used, the emulsifier may have a hydrophilic-lipophilic balance (HLB) of less than 10.

The compositions described herein are stable. In one aspect, stability refers to the integrity of the composition as a whole, and in particular, the stability of the nanodroplets in the petrolatum. Under ambient conditions, the petrolatum and the one or more anti-fungal agents and optional cationic biocides will not separate for greater than two years, meaning that the composition is shelf stable for at least two years. Even under accelerated conditions, such as reduced pressure, the petrolatum and the one or more anti-fungal agents and optional cationic biocides do not separate, but rather the one or more anti-fungal agents and optional cationic biocides remain suspended as nanodroplets in the petrolatum. In addition to the stability of the nanodroplets within the composition, the compositions described herein also show exceptional chemical stability for the one or more anti-fungal agents and optional cationic biocides. The chemical stability stems primarily from the low-temperature manufacturing process described below. The absence of excessive heat conditions in the manufacturing of the compositions improves the chemical stability (resistance to degradation) for the one or more anti-fungal agents and optional cationic biocides.

According to at least one aspect of the present disclosure, the petrolatum-based compositions described herein consist essentially of petrolatum, one or more anti-fungal agents, and water. In at least one embodiment, the petrolatum-based compositions consist essentially of petrolatum, one or more anti-fungal agents, benzalkonium chloride, and water. In alternative embodiments, the petrolatum-based compositions described herein consist of petrolatum, a cationic biocide, and one or more anti-fungal agents.

In other embodiments, the petrolatum-based compositions described herein may further comprise a compound that stimulates healing. More specifically, the petrolatum-based compositions described herein may further comprise a compound that stimulates healing for use in intraoperative applications and chronic wound care applications. Non-limiting examples of compounds that stimulate healing include polycaprolactone-tricalcium phosphate (PCL-TCP), collagen, chitosan, cellulose, thrombin, chondroitin sulfate (CS), chondroitin sulfate succinimidyl succinate (CS-NHS), and growth factors such as TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, or autologous intraoperative biologics such as platelet-rich plasma (PRP) and bone marrow (BM).

In other embodiments, the petrolatum-based compositions described herein may further comprise a dermatologically acceptable carrier. A "dermatologically-acceptable carrier," as used herein, is a component or components suitable for use in contact with human keratinous tissue without undue toxicity, incompatibility, instability, allergic response, and the like. Where employed, the carrier is inert in the sense of not bringing about a deactivation of the active ingredients, and in the sense of not bringing about any adverse effect on the skin areas to which it is applied. Common dermatological additives are also envisioned for some embodiments. In certain embodiments, a dermatological additive is a whitening agent and/or hemostatic agent.

Additionally, the presently-disclosed compositions may be incorporated in predetermined therapeutically effective amounts into disposables such as wipes, gauze, patches, wraps, bandages, adhesive strips, sponge, cotton swab, glove, sock, wrist bands, fabric, fibers, sutures, medication pad, underwear, tissue, pain-relief gel pack or bed liner and the like. For instance, the composition may be applied to the surface of, or impregnated into disposables.

II. Process for Making

The present disclosure also provides a method for making the compositions described in Section (I). The process comprises: (a) dissolving one or more anti-fungal agents in a solvent to give an anti-fungal agent solution; (b) heating the petrolatum to a temperature sufficient to give a melted petrolatum, and heating the anti-fungal agent solution to a temperature higher than the temperature of the petrolatum to give a heated anti-fungal agent solution; (c) mixing the melted petrolatum and the heated anti-fungal agent solution to give a melted mixture; and, (d) cooling the melted mixture to give the petrolatum-based composition. As would be appreciated by one of skill in the art, steps (a)-(d) are conducted sequentially.

The one or more anti-fungal agents as well the optional cationic biocide, selected from the group described in Section (I), is first dissolved in a solvent to give a anti-fungal agent solution. Acceptable solvents for the anti-fungal agent solution include water or other solvents. Generally polar solvents are used. The anti-fungal agents and optional cationic biocides are typically dissolved in the solvent a concentration ranging from about 0.05% to about 5%. Typically, the amount of solvent used is from about 1:10 to about 1:30 the amount of petrolatum and more preferably is about 1:20 to the amount of petrolatum by volume. The amount of one or more anti-fungal agents and optional cationic biocides can be calculated by one skilled in the art to provide the desired weight percentage for the final composition.

Both the anti-fungal agent solution and the petrolatum are heated. The heating of these two ingredients can be conducted at the same time or sequentially so long as the melted petrolatum and the heated anti-fungal agent solution are at the appropriate temperatures during the mixing step. Petrolatum is a solid that melts at approximately 37° C. As such, petrolatum may be heated to any temperature at or above 37°

C. For instance, the petrolatum may be heated to a temperature ranging from about 37° C. to about 45° C., from about 40° C. to about 50° C., from about 45° C. to about 55° C., from about 50° C. to about 60° C., from about 55° C. to about 65° C., from about 60° C. to about 70° C., from about 65° C. to about 75° C., from about 70° C. to about 80° C., from about 75° C. to about 85° C., from about 80° C. to about 90° C., from about 85° C. to about 95° C., or from about 90° C. to about 100° C. or more. Higher temperatures may also be envisioned. Preferably, the petrolatum is heated to a temperature ranging from about 37° C. to about 55° C., more preferably to a temperature ranging from about 40° C. to about 50° C. Heat may be provided to the petrolatum by any method known in the art, but a water bath or low temperature hot plate are preferred.

The anti-fungal agent solution is heated to a temperature above the temperature of the melted petrolatum. Any temperature above the temperature of the melted petrolatum may be used in a method of the present disclosure, provided that the heat does not cause excessive degradation of an active ingredient such as the one or more anti-fungal agents, or excessive evaporation of the active ingredient or polar solvent. For instance, the anti-fungal agent solution may be heated to a temperature that is about 1° C. to about 10° C., about 5° C. to about 15° C., about 10° C. to about 20° C., about 15° C. to about 25° C., about 20° C. to about 30° C., about 25° C. to about 35° C., about 30° C. to about 40° C., about 35° C. to about 45° C., about 40° C. to about 50° C., about 45° C. to about 55° C., about 50° C. to about 60° C. or about 65° C. or about 75° C. higher than the temperature of the melted petrolatum. Higher temperatures may also be envisioned. Preferably, the anti-fungal agent solution is heated to a temperature that is about 1° C. to about 10° C. higher than the temperature of the melted petrolatum. In another embodiment, the anti-fungal agent solution is heated to a temperature that is about 1° C. to about 5° C. higher than the melted petrolatum. In still other embodiments, the anti-fungal agent solution is heated to a temperature that is about 1° C., 2° C., 3° C., 4° C., or 5° C. above the temperature of the melted petrolatum. Again, the heating can be provided by any means known in the art but is preferably provided by a water bath or low temperature hot plate.

Once both the petrolatum and the anti-fungal agent solution are heated as described above, the melted petrolatum and the heated anti-fungal agent solution are mixed to give a melted mixture containing petrolatum and the heated anti-fungal agent solution. The mixing can be accomplished by a variety of methods including homogenization, acoustic mixing, and high RPM mixing. Depending on the batch size, the size of the mixer, and the type of mixing, the mixing may be conducted for several minutes or more. When mixed in accordance with the parameters disclosed above, the melted petrolatum and the heated anti-fungal agent solution fuse in the melted mixture.

After the melted petrolatum and the heated anti-fungal agent solution have fused they are allowed to cool and solidify into the composition described more fully in Section (I) ("the final composition"). Cooling may be achieved by reducing the amount of heat provided to the melted mixture, or cooling may be achieved passively under conditions where no heating is added. In some embodiments, cooling is controlled so that the temperature of the melting mixture is gradually lowered to ambient temperatures. The product is preferably packaged a few degrees above its solidification point so that the packaging can be filled by pouring the melted mixture. The composition preferably solidifies to the final composition in the package. The package is sealed after this solidification.

The process may be conducted with one or more anti-fungal agents, and optionally, one or more cationic biocides. The anti-fungal agents and optionally the cationic biocides may be dissolved in s solvent separately or may be dissolved in the same solvent. The addition of additional anti-fungal agents or optional cationic biocides does not change the process steps above.

III. Methods of Use

In another aspect, the invention encompasses a method of preventing or treating onychomycosis in a subject using the compositions described herein.

The compositions may be applied topically to the nail of a subject in need. Subjects in need may be those having onychomycosis, including subjects having distal subungual onychomycosis, white superficial onychomycosis (WSO), proximal subungual onychomycosis, and Candidal onychomycosis. The onychomycosis may be caused by, for example, *Trichophyton rubrum* (*T. rubrum*) or *Candida auris* (*C. auris*), including multi-drug resistant *C. auris*. The subject is preferably human but the composition may also be useful in animals, particularly mammals, for example domestic animals, livestock, or other types of animals.

Typically, the composition is applied to the nail of the subject. Application to the nail includes application to a site having onychomycosis as well as to sites that may be susceptible to acquiring onychomycosis. Therefore, the presently disclosed compositions may be applied to skin or nails in order to prevent infection by the causative agent responsible for onychomycosis. The presently disclosed compositions may also be used as a topical dressing to a nail and/or skin of a subject in order to prevent or reduce the occurrence of onychomycosis. As used herein, the terms "applied to the nail" or "applying to the nail," in all their forms, as used throughout this disclosure in reference to applying the presently disclosed compositions to the nail of a subject, refers to all modes of administration of the compositions to the nail and/or nearby skin of a patient including topical administration of the compositions directly to the nail or surrounding skin of a subject or causing contact between the compositions and the nail of a subject through, for instance, a wrap, gauze, or bandage impregnated or containing the presently disclosed compositions.

The amount of composition applied in the methods described herein can and will vary depending on the condition being treated and the severity of that condition. Generally, the amount used is sufficient to cover the affected nail area with a thin layer of the composition. The composition is applied directly to the nail. In some embodiments, the composition is spread so that it forms a thin layer over the treatment area. In other embodiments, the composition is spread by a melting action that occurs as the warmth of the patient's nail and surrounding skin melts the petrolatum or pharmaceutically acceptable carrier. The composition may be covered with a bandage after application. The compositions may also be impregnated into a bandage or other material that is applied to the treatment area.

The composition when applied to the nail and surrounding skin is non-irritating and non-cytotoxic. These properties allow the composition to be used on sensitive treatment areas. These characteristics also allow for use to treat or prevent onychomycosis over a long period, such as for example 2 weeks, 4 weeks, 6 weeks, 8 weeks, or longer without irritation to the treated area. It will be recognized however, that the compositions may be used for shorter periods of time if necessary.

The compositions are also capable of extended release of the one or more anti-fungal agents and optionally cationic biocides to the area of application. "Extended release" as used herein means that the compositions release anti-fungal agents and optionally cationic biocides to the application site over a period of time extending past twelve hours. The time over which the extended release is provided is variable depending on the amount of the composition that is applied, but in general, the release of anti-fungal agents and optional cationic biocides is extended beyond the initial application and anti-fungal agents and optional cationic biocides has been shown to be released for up to 1 week. This extended release allows the composition to be applied less frequently and improves patient compliance with the treatment.

The compositions of the present disclosure also offer kinetic release when applied to the skin or nails. Kinetic release means that the anti-fungal agents and optional cationic biocides are released to the treatment area more rapidly when the treatment area is hotter.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Exemplary Formulation Process: Petrolatum-Based Terbinafine HCl Composition

Formulation 1 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Terbinafine HCl and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Terbinafine HCl, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 2

Petrolatum-Based Compositions Comprising Terbinafine HCl

Formulation 2 is prepared in accordance with the present disclosure by mixing Terbinafine HCl and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Terbinafine HCl composition is formed, which comprises from about 0.01% to about 5% by weight terbinafine HCl and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 3

Topical Administration of Petrolatum-Based Compositions Comprising Terbinafine HCl Improves Clinical Outcomes in Subjects Having Onychomycosis The effect of topical administration of Formulations 1 and 2 (petrolatum-based compositions comprising Terbinafine HCl) in the treatment of human subjects having onychomycosis will be studied using a randomized, double-blind clinical study. During the clinical study, a group of human subjects will be topically administered the compositions corresponding to Formulations 1 and 2 of Examples 1 and 2. In particular, the petrolatum-based compositions comprising Terbinafine HCl will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis subtypes of onychomycosis.

Example 4

Exemplary Formulation Process: Petrolatum-Based Ciclopirox Composition

Formulation 3 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Ciclopirox and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Ciclopirox, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 5

Petrolatum-Based Compositions Comprising Ciclopirox

Formulation 4 is prepared in accordance with the present disclosure by mixing Ciclopirox and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Ciclopirox composition is formed, which comprises from about 0.01% to about 5% by weight Ciclopirox and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 6

Topical Administration of Petrolatum-Based Compositions Comprising Ciclopirox Improves Clinical Outcomes in Subjects Having Onychomycosis The effect of topical administration of Formulations 3 and 4 (petrolatum-based compositions comprising Ciclopirox) in the treatment of human subjects having onychomycosis will be studied using a randomized, double-blind clinical study. During the clinical study, a group of human subjects will be topically administered the compositions corresponding to Formulations 3 and 4 of Examples 4 and 5. In particular, the petrolatum-based compositions comprising Ciclopirox will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 7

Exemplary Formulation Process: Petrolatum-Based Ciclopirox Olamine Composition

Formulation 5 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Ciclopirox Olamine and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Ciclopirox Olamine, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 8

Petrolatum-Based Compositions Comprising Ciclopirox Olamine

Formulation 6 is prepared in accordance with the present disclosure by mixing Ciclopirox Olamine and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Ciclopirox Olamine composition is formed, which comprises from about 0.01% to about 5% by weight Ciclopirox Olamine and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 9

Topical Administration of Petrolatum-Based Compositions Comprising Ciclopirox Olamine Improves Clinical Outcomes in Subjects Having Onychomycosis The effect of topical administration of Formulations 5 and 6 (petrolatum-based compositions comprising Ciclopirox Olamine) in the treatment of human subjects having onychomycosis will be studied using a randomized, double-blind clinical study. During the clinical study, a group of human subjects will be topically administered the compositions corresponding to Formulations 5 and 6 of Examples 7 and 8. In particular, the petrolatum-based compositions comprising Ciclopirox Olamine will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by $T.$ $rubrum$, $Candida$, as well as for the distal subungual onychomycosis, white superficial onychomycosis (WSO), proximal subungual onychomycosis, and Candidal onychomycosis sub-types of onychomycosis.

Example 10

Exemplary Formulation Process: Petrolatum-Based Fluconazole Composition

Formulation 7 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Fluconazole and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Fluconazole, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 11

Petrolatum-Based Compositions Comprising Fluconazole

Formulation 8 is prepared in accordance with the present disclosure by mixing Fluconazole and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Fluconazole composition is formed, which comprises from about 0.01% to about 5% by weight Fluconazole and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 12

Topical Administration of Petrolatum-Based Compositions Comprising Fluconazole Improves Clinical Outcomes in Subjects Having Onychomycosis The effect of topical administration of Formulations 7 and 8 (petrolatum-based compositions comprising Fluconazole) in the treatment of human subjects having onychomycosis will be studied using a randomized, double-blind clinical study. During the clinical study, a group of human subjects will be topically administered the compositions corresponding to Formulations 7 and 8 of Examples 10 and 11. In particular, the petrolatum-based compositions comprising Fluconazole will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by $T.$ $rubrum$, $Candida$, as well as for the distal subungual onychomycosis, white superficial onychomycosis (WSO), proximal subungual onychomycosis, and Candidal onychomycosis sub-types of onychomycosis.

Example 13

Exemplary Formulation Process: Petrolatum-Based Itraconazole Composition

Formulation 9 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Itraconazole and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Itraconazole, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 14

Petrolatum-Based Compositions Comprising Itraconazole

Formulation 10 is prepared in accordance with the present disclosure by mixing Itraconazole and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Itraconazole composition is formed, which comprises from about 0.01% to about 5% by weight Itraconazole and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 15

Topical Administration of Petrolatum-Based Compositions Comprising Itraconazole Improves Clinical Outcomes in Subjects Having Onychomycosis The effect of topical administration of Formulations 9 and 10 (petrolatum-based compositions comprising Itraconazole) in the treatment of human subjects having onychomycosis will be studied using a randomized, double-blind clinical study. During the clinical study, a group of human subjects will be topically administered the compositions corresponding to Formulations 9 and 10 of Examples 13 and 14. In particular, the petrolatum-based compositions comprising Itraconazole will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 16

Exemplary Formulation Process: Petrolatum-Based Ketoconazole Composition

Formulation 11 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Ketoconazole and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Ketoconazole, 0.13% BZK and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 17

Petrolatum-Based Compositions Comprising Ketoconazole

Formulation 12 is prepared in accordance with the present disclosure by mixing Ketoconazole and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Ketoconazole composition is formed, which comprises from about 0.01% to about 5% by weight Ketoconazole and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 18

Topical Administration of Petrolatum-Based Compositions Comprising Ketoconazole Improves Clinical Outcomes in Subjects Having Onychomycosis The effect of topical administration of Formulations 11 and 12 (petrolatum-based compositions comprising Ketoconazole) in the treatment of human subjects having onychomycosis will be studied using a randomized, double-blind clinical study. During the clinical study, a group of human subjects will be topically administered the compositions corresponding to Formulations 11 and 12 of Examples 16 and 17. In particular, the petrolatum-based compositions comprising Ketoconazole will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 19

Exemplary Formulation Process: Petrolatum-Based Amorolfine Composition

Formulation 13 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Amorolfine and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Amorolfine, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 20

Petrolatum-Based Compositions Comprising Amorolfine

Formulation 14 is prepared in accordance with the present disclosure by mixing Amorolfine and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Amorolfine composition is formed, which comprises from about 0.01% to about 5% by weight Amorolfine and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 21

Topical Administration of Petrolatum-Based Compositions Comprising Amorolfine Improves Clinical Outcomes in Subjects Having Onychomycosis The effect of topical administration of Formulations 13 and 14 (petrolatum-based compositions comprising Amorolfine) in the treatment of human subjects having onychomycosis will be studied using a randomized, double-blind clinical study. During the clinical study, a group of human subjects will be topically administered the compositions corresponding to Formulations 13 and 14 of Examples 19 and 20. In particular, the petrolatum-based compositions comprising Amorolfine will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T.*

*rubrum, Candida*, as well as for the distal subungual onychomycosis, white superficial onychomycosis (WSO), proximal subungual onychomycosis, and Candidal onychomycosis sub-types of onychomycosis.

Example 22

Exemplary Formulation Process: Petrolatum-Based Efinaconazole Composition

Formulation 15 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Efinaconazole and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Efinaconazole, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 23

Petrolatum-Based Compositions Comprising Efinaconazole

Formulation 16 is prepared in accordance with the present disclosure by mixing Efinaconazole and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Efinaconazole composition is formed, which comprises from about 0.01% to about 5% by weight Efinaconazole and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 24

Topical Administration of Petrolatum-Based Compositions Comprising Efinaconazole Improves Clinical Outcomes in Subjects Having Onychomycosis The effect of topical administration of Formulations 15 and 16 (petrolatum-based compositions comprising Efinaconazole) in the treatment of human subjects having onychomycosis will be studied using a randomized, double-blind clinical study. During the clinical study, a group of human subjects will be topically administered the compositions corresponding to Formulations 15 and 16 of Examples 22 and 23. In particular, the petrolatum-based compositions comprising Efinaconazole will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 25

Exemplary Formulation Process: Petrolatum-Based Clotrimazole Composition

Formulation 17 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Clotrimazole and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Clotrimazole, 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 26

Petrolatum-Based Compositions Comprising Clotrimazole

Formulation 18 is prepared in accordance with the present disclosure by mixing Clotrimazole and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Clotrimazole composition is formed, which comprises from about 0.01% to about 5% by weight Clotrimazole and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 27

Topical Administration of Petrolatum-Based Compositions Comprising Clotrimazole Improves Clinical Outcomes in Subjects Having Onychomycosis The effect of topical administration of Formulations 17 and 18 (petrolatum-based compositions comprising Clotrimazole) in the treatment of human subjects having onychomycosis will be studied using a randomized, double-blind clinical study. During the clinical study, a group of human subjects will be topically administered the compositions corresponding to Formulations 17 and 18 of Examples 25 and 26. In particular, the petrolatum-based compositions comprising Clotrimazole will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 28

Exemplary Formulation Process: Petrolatum-Based Miconazole (Miconazole Nitrate) Composition Formulation 19 is prepared by adding 2540.3 pounds of white petrolatum to a tank that has been cleaned and sterilized. The petrolatum in the tanks is heated to 110° C. to 113° F. in order to cause the petrolatum to melt. In a separate clean and sanitized container 133.70 pounds of water is mixed with Miconazole (Miconazole Nitrate) and BZK to form an anti-fungal agent solution. The anti-fungal agent solution is heated to 122° F. With the melted petrolatum at a temperature from about 110° F. to about 113° F. and the anti-fungal agent solution at a temperature of 122° F., the anti-fungal agent solution is slowly added to the petrolatum while mixing. After all of the anti-fungal solution is added to the melted petrolatum at temperature, the heat is decreased slowly to from about 96° F. to about 104° F. The resulting formulation contains the following ingredients by weight percent: 95% petrolatum, 0.2% Miconazole (Miconazole Nitrate), 0.13% BZK, and 4.67% water. The formulation is observed to be stable for at least 6 months. During the 6 month observation period, the anti-fungal solution remains substantially suspended in the petrolatum carrier thereby resulting in a composition suitable for therapeutic use for the treatment of onychomycosis by topical administration to the nail and surrounding skin of a subject in need thereof.

Example 29

Petrolatum-Based Compositions Comprising Miconazole (Miconazole Nitrate)

Formulation 20 is prepared in accordance with the present disclosure by mixing Miconazole (Miconazole Nitrate) and water to form an anti-fungal agent solution. The anti-fungal agent solution is heated to a temperature from about 1° C. to about 5° C. higher than the temperature of the melted petrolatum and mixed. Upon allowing the mixture to cool, a stable petrolatum-based Miconazole (Miconazole Nitrate) composition is formed, which comprises from about 0.01% to about 5% by weight Miconazole (Miconazole Nitrate) and greater than 85% petrolatum. Optionally, one or more cationic biocides is added to the anti-fungal agent solution prior to mixing with the melted petrolatum such that the resultant stable petrolatum-based composition further includes from about 0.001% to about 0.15% cationic biocide. Such cationic biocides may include, for example, benzalkonium chloride, cetrimide, chlorhexidine, and any combination thereof.

Example 30

Topical Administration of Petrolatum-Based Compositions Comprising Miconazole (Miconazole Nitrate) Improves Clinical Outcomes in Subjects Having Onychomycosis The effect of topical administration of Formulations 19 and 20 (petrolatum-based compositions comprising Miconazole (Miconazole Nitrate)) in the treatment of human subjects having onychomycosis will be studied using a randomized, double-blind clinical study. During the clinical study, a group of human subjects will be topically administered the compositions corresponding to Formulations 19 and 20 of Examples 28 and 29. In particular, the petrolatum-based compositions comprising Miconazole (Miconazole Nitrate) will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Statements of the Disclosure:

Numerous examples are provided herein to enhance understanding of the present disclosure. A specific set of statements are provided as follows.

Statement 1: A method of treating onychomycosis in a subject, the method comprising applying a petrolatum-based composition to the nail of a subject in need of treatment, wherein the petrolatum-based composition comprises one or more anti-fungal agents and a petrolatum carrier.

Statement 2: The method according to Statement 2, wherein the one or more anti-fungal agents is dispersed in the petrolatum carrier to form a stable petrolatum-based suspension.

Statement 3: The method according to Statement 1 or Statement 2, wherein the one or more anti-fungal agents is dispersed in the petrolatum carrier in the form of nanodroplets.

Statement 4: The method according to any one of Statements 1-3, wherein the petrolatum-based composition comprises nanodroplets dispersed in the petrolatum carrier, wherein the nanodroplets comprises one or more fungal agents and a polar solvent.

Statement 5: The method according to any one of Statements 1-4, wherein the one or more anti-fungal agents is dissolved in a polar solvent to form an anti-fungal agent solution, the anti-fungal agent solution dispersed in the petrolatum to form a stable suspension.

Statement 6: The method according to Statement 5, wherein the anti-fungal agent solution is dispersed in the petrolatum in the form of nanodroplets.

Statement 7: The method according to any one of Statements 1-6, wherein the one or more anti-fungal agents is selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof.

Statement 8: The method according to any one of Statements 1-7, wherein the onychomycosis is caused by *Trichophyton rubrum (T. rubrum)*.

Statement 9: The method according to any one of Statements 1-7, wherein the onychomycosis is caused by *Candida*.

Statement 10: The method according to any one of Statements 1-7, wherein the onychomycosis is distal subungual onychomycosis.

Statement 11: The method according to any one of Statements 1-7, wherein the onychomycosis is white superficial onychomycosis (WSO).

Statement 12: The method according to any one of Statements 1-7, wherein the onychomycosis is proximal subungual onychomycosis.

Statement 13: The method according to any one of Statements 1-7, wherein the onychomycosis is Candidal onychomycosis.

Statement 14: The method according to Statement 13, wherein the Candidal onychomycosis is caused by *Candida auris (C. auris)*.

Statement 15: The method according to Statement 14, wherein the *C. auris* is multi-drug resistant *C. auris*.

Statement 16: The method according to any one of Statements 1-15, wherein the one or more anti-fungal agents comprises from about 0.05% to about 5% by weight of the petrolatum-based composition.

Statement 17: The method according to any one of Statements 1-15, wherein the one or more anti-fungal agents comprises from about 0.05% to about 3% by weight of the petrolatum-based composition.

Statement 18: The method according to any one of Statements 1-15, wherein the one or more anti-fungal agents comprises from about 0.1% to about 1% by weight of the petrolatum-based composition.

Statement 19: The method according to any one of Statements 1-15, wherein the one or more anti-fungal agents comprises from about 0.2% to about 0.6% by weight of the petrolatum-based composition.

Statement 20: The method according to any one of Statements 1-15, wherein the one or more anti-fungal agents comprises from about 0.3% to about 0.5% by weight of the petrolatum-based composition.

Statement 21: The method according to any one of Statements 1-15, wherein the one or more anti-fungal agents comprises from about 0.1% to about 3.5% by weight of the petrolatum-based composition.

Statement 22: The method according to any one of Statements 1-15, wherein the one or more anti-fungal agents comprises from about 0.05% to about 2.5% by weight of the petrolatum-based composition.

Statement 23: The method according to any one of Statements 1-15, wherein the one or more anti-fungal agents comprises from about 0.5% to about 3% by weight of the petrolatum-based composition.

Statement 24: The method according to any one of Statements 1-15, wherein the one or more anti-fungal agents comprises from about 0.5% to about 2.5% by weight of the petrolatum-based composition.

Statement 25: The method according to any one of Statements 1-15, wherein the one or more anti-fungal agents comprises from about 1.5% to about 2.5% by weight of the petrolatum-based composition.

Statement 26: The method according to any one of Statements 1-25, wherein the petrolatum-based composition comprises greater than about 80% by weight petrolatum.

Statement 27: The method according to any one of Statements 1-25, wherein the petrolatum-based composition comprises greater than about 90% by weight petrolatum.

Statement 28: The method according to any one of Statements 1-25, wherein the petrolatum-based composition comprises greater than about 95% by weight petrolatum.

Statement 29: The method according to any one of Statements 1-28, wherein the petrolatum-based composition contains no emulsifier.

Statement 30: The method according to any one of Statements 1-28, wherein the petrolatum-based composition excludes an added emulsifier.

Statement 31: The method according to any one of Statements 1-30, wherein the petrolatum-based composition further includes a cationic biocide selected from the group consisting of benzalkonium chloride, cetrimide, chlorhexidine, and any combination thereof.

Statement 32: The method according to Statement 31, wherein the petrolatum-based composition comprises from about 0.001% to about 0.15% by weight benzalkonium chloride (BZK).

Statement 33: The method according to Statement 31, wherein the petrolatum-based composition comprises from about 0.001% to about 0.01% or from about 0.005% to about 0.007% by weight benzalkonium chloride (BZK).

Statement 34: The method according to any one of Statements 1-33, wherein the petrolatum-based composition is prepared by a process comprising: a) dissolving the one or more anti-fungal agents in a polar solvent to give an anti-fungal agent solution; b) heating the petrolatum to a temperature sufficient to cause the petrolatum to melt to give a melted petrolatum and heating the anti-fungal agent solution to a temperature higher than the temperature of the melted petrolatum to give a heated anti-fungal agent solution; c) mixing the melted petrolatum and the heated anti-fungal agent solution to give a melted mixture; and d) cooling the melted mixture to give the petrolatum-based composition.

Statement 35: The method according to Statement 34, wherein the heated anti-fungal agent solution has a temperature that is about 1° C. to about 5° C. higher than the temperature of the melted petrolatum.

Statement 36: The method according to any one of Statements 1-35, wherein the petrolatum-based composition comprises from about 0.01% to about 5% by weight terbinafine HCl.

Statement 37: The method according to any one of Statements 1-35, wherein the petrolatum-based composition comprises from about 0.01% to about 5% by weight ciclopirox.

Statement 38: The method according to any one of Statements 1-35, wherein the petrolatum-based composition comprises from about 0.01% to about 5% by weight ciclopirox olamine.

Statement 39: The method according to any one of Statements 1-35, wherein the petrolatum-based composition comprises from about 0.01% to about 5% by weight fluconazole.

Statement 40: The method according to any one of Statements 1-35, wherein the petrolatum-based composition comprises from about 0.01% to about 5% by weight itraconazole.

Statement 41: The method according to any one of Statements 1-35, wherein the petrolatum-based composition comprises from about 0.01% to about 5% by weight ketoconazole.

Statement 42: The method according to any one of Statements 1-35, wherein the petrolatum-based composition comprises from about 0.01% to about 5% by weight amorolfine.

Statement 43: The method according to any one of Statements 1-35, wherein the petrolatum-based composition comprises from about 0.01% to about 5% by weight efinaconazole.

Statement 44: A petrolatum-based composition for the treatment of onychomycosis, the composition comprising a pharmaceutically effective amount of one or more anti-fungal agents in a petrolatum carrier.

Statement 45: The composition according to Statement 44, wherein the one or more anti-fungal agents is dispersed in the petrolatum carrier to form a stable petrolatum-based suspension.

Statement 46: The composition according to Statement 44 or Statement 45, wherein the one or more anti-fungal agents is dispersed in the petrolatum carrier in the form of nanodroplets.

Statement 47: The composition according to any one of Statements 44-46, wherein the petrolatum-based composition comprises nanodroplets dispersed in the petrolatum carrier, wherein the nanodroplets comprises one or more fungal agents and a polar solvent.

Statement 48: The composition according to any one of Statements 44-47, wherein the one or more anti-fungal agents is dissolved in a polar solvent to form an anti-fungal agent solution, the anti-fungal agent solution dispersed in the petrolatum to form a stable suspension.

Statement 49: The composition according to Statement 48, wherein the anti-fungal agent solution is dispersed in the petrolatum in the form of nanodroplets.

Statement 50: The composition according to any one of Statements 44-49, wherein the one or more anti-fungal agents is selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof.

Statement 51: The composition according to any one of Statements 44-50, wherein the onychomycosis is caused by *Trichophyton rubrum* (*T. rubrum*).

Statement 52: The composition according to any one of Statements 44-50, wherein the onychomycosis is caused by *Candida*.

Statement 53: The composition according to any one of Statements 44-50, wherein the onychomycosis is distal subungual onychomycosis.

Statement 54: The composition according to any one of Statements 44-50, wherein the onychomycosis is white superficial onychomycosis (WSO).

Statement 55: The composition according to any one of Statements 44-50, wherein the onychomycosis is proximal subungual onychomycosis.

Statement 56: The composition according to any one of Statements 44-50, wherein the onychomycosis is Candidal onychomycosis.

Statement 57: The composition according to Statement 56, wherein the Candidal onychomycosis is caused by *Candida auris* (*C. auris*).

Statement 58: The composition according to Statement 57, wherein the *C. auris* is multi-drug resistant *C. auris*.

Statement 59: The composition according to any one of Statements 44-58, wherein the one or more anti-fungal agents comprises from about 0.05% to about 5% by weight of the petrolatum-based composition.

Statement 60: The composition according to any one of Statements 44-58, wherein the one or more anti-fungal agents comprises from about 0.05% to about 3% by weight of the petrolatum-based composition.

Statement 61: The composition according to any one of Statements 44-58, wherein the one or more anti-fungal agents comprises from about 0.1% to about 1% by weight of the petrolatum-based composition.

Statement 62: The composition according to any one of Statements 44-58, wherein the one or more anti-fungal agents comprises from about 0.2% to about 0.6% by weight of the petrolatum-based composition.

Statement 63: The composition according to any one of Statements 44-58, wherein the one or more anti-fungal agents comprises from about 0.3% to about 0.5% by weight of the petrolatum-based composition.

Statement 64: The composition according to any one of Statements 44-58, wherein the one or more anti-fungal agents comprises from about 0.1% to about 3.5% by weight of the petrolatum-based composition.

Statement 65: The composition according to any one of Statements 44-58, wherein the one or more anti-fungal agents comprises from about 0.05% to about 2.5% by weight of the petrolatum-based composition.

Statement 66: The composition according to any one of Statements 44-58, wherein the one or more anti-fungal agents comprises from about 0.5% to about 3% by weight of the petrolatum-based composition.

Statement 67: The composition according to any one of Statements 44-58, wherein the one or more anti-fungal agents comprises from about 0.5% to about 2.5% by weight of the petrolatum-based composition.

Statement 68: The composition according to any one of Statements 44-58, wherein the one or more anti-fungal agents comprises from about 1.5% to about 2.5% by weight of the petrolatum-based composition.

Statement 69: The composition according to any one of Statements 44-68, wherein the petrolatum-based composition comprises greater than about 80% by weight petrolatum.

Statement 70: The composition according to any one of Statements 44-68, wherein the petrolatum-based composition comprises greater than about 90% by weight petrolatum.

Statement 71: The composition according to any one of Statements 44-68, wherein the petrolatum-based composition comprises greater than about 95% by weight petrolatum.

Statement 72: The composition according to any one of Statements 44-71, wherein the petrolatum-based composition contains no emulsifier.

Statement 73: The composition according to any one of Statements 44-71, wherein the petrolatum-based composition excludes an added emulsifier.

Statement 74: The composition according to any one of Statements 44-73, wherein the petrolatum-based composition further includes a cationic biocide selected from the group consisting of benzalkonium chloride, cetrimide, chlorhexidine, and any combination thereof.

Statement 75: The composition according to Statement 74, wherein the petrolatum-based composition comprises from about 0.001% to about 0.15% by weight benzalkonium chloride (BZK).

Statement 76: The composition according to Statement 74, wherein the petrolatum-based composition comprises from about 0.001% to about 0.01% or from about 0.005% to about 0.007% by weight benzalkonium chloride (BZK).

Statement 77: The composition according to any one of Statements 44-76, wherein the petrolatum-based composition is prepared by a process comprising: a) dissolving the one or more anti-fungal agents in a polar solvent to give an anti-fungal agent solution; b) heating the petrolatum to a temperature sufficient to cause the petrolatum to melt to give a melted petrolatum and heating the anti-fungal agent solution to a temperature higher than the temperature of the melted petrolatum to give a heated anti-fungal agent solution; c) mixing the melted petrolatum and the heated anti-fungal agent solution to give a melted mixture; and d) cooling the melted mixture to give the petrolatum-based composition.

Statement 78: The composition according to Statement 77, wherein the heated anti-fungal agent solution has a temperature that is about 1° C. to about 5° C. higher than the temperature of the melted petrolatum.

Statement 79: The composition according to any one of Statements 44-78, wherein the petrolatum-based composition comprises from about 0.01% to about 5% by weight terbinafine HCl.

Statement 80: The composition according to any one of Statements 44-78, wherein the petrolatum-based composition comprises from about 0.01% to about 5% by weight ciclopirox.

Statement 81: The composition according to any one of Statements 44-78, wherein the petrolatum-based composition comprises from about 0.01% to about 5% by weight ciclopirox olamine.

Statement 82: The composition according to any one of Statements 44-78, wherein the petrolatum-based composition comprises from about 0.01% to about 5% by weight fluconazole.

Statement 83: The composition according to any one of Statements 44-78, wherein the petrolatum-based composition comprises from about 0.01% to about 5% by weight itraconazole.

Statement 84: The composition according to any one of Statements 44-78, wherein the petrolatum-based composition comprises from about 0.01% to about 5% by weight ketoconazole.

Statement 85: The composition according to any one of Statements 44-78, wherein the petrolatum-based composition comprises from about 0.01% to about 5% by weight amorolfine.

Statement 86: The composition according to any one of Statements 44-78, wherein the petrolatum-based composition comprises from about 0.01% to about 5% by weight efinaconazole.

Statement 87: The composition according to any one of Statements 44-78, wherein the petrolatum-based composition comprises from about 0.01% to about 5% by weight clotrimazole.

Statement 88: The composition according to any one of Statements 44-78, wherein the petrolatum-based composition comprises from about 0.01% to about 5% by weight miconazole (miconazole nitrate).

Statement 89: The method according to any one of Statements 1-35, wherein the petrolatum-based composition comprises from about 0.01% to about 5% by weight clotrimazole.

Statement 90: The method according to any one of Statements 1-35, wherein the petrolatum-based composition comprises from about 0.01% to about 5% by weight miconazole (miconazole nitrate).

What is claimed is:

1. A method of treating onychomycosis in a subject, the method comprising applying a petrolatum-based composition to the nail of a subject in need of treatment, wherein the petrolatum-based composition comprises one or more anti-fungal agents and a petrolatum carrier, and wherein the petrolatum-based composition comprises greater than about 90% by weight petrolatum.

2. The method according to claim 1, wherein the one or more anti-fungal agents is dispersed in the petrolatum carrier to form a stable petrolatum-based suspension.

3. The method according to claim 2, wherein the one or more anti-fungal agents is dissolved in a polar solvent to form an anti-fungal agent solution, the anti-fungal agent solution dispersed in the petrolatum to form a stable suspension.

4. The method according to claim 1, wherein the one or more anti-fungal agents is selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof.

5. The method according to claim 1, wherein the onychomycosis is caused by *Trichophyton rubrum* (*T. rubrum*).

6. The method according to claim 1, wherein the onychomycosis is caused by *Candida*.

7. The method according to claim 6, wherein the Candidal onychomycosis is caused by *Candida auris* (*C. auris*).

8. The method according to claim 1, wherein the one or more anti-fungal agents comprises from about 0.5% to about 2.5% by weight of the petrolatum-based composition.

9. The method according to claim 1, wherein the petrolatum-based composition excludes an added emulsifier.

10. The method according to claim 9, wherein the petrolatum-based composition further includes a cationic biocide selected from the group consisting of benzalkonium chloride, cetrimide, chlorhexidine, and any combination thereof.

11. The method according to claim 9, wherein the petrolatum-based composition comprises from about 0.001% to about 0.15% by weight benzalkonium chloride (BZK).

12. The method according to claim 1, wherein the petrolatum-based composition is prepared by a process comprising:
a) dissolving the one or more anti-fungal agents in a polar solvent to give an anti-fungal agent solution;
b) heating the petrolatum to a temperature sufficient to cause the petrolatum to melt to give a melted petrolatum and heating the anti-fungal agent solution to a temperature higher than the temperature of the melted petrolatum to give a heated anti-fungal agent solution;
c) mixing the melted petrolatum and the heated anti-fungal agent solution to give a melted mixture; and
d) cooling the melted mixture to give the petrolatum-based composition.

13. The method according to claim 12, wherein the heated anti-fungal agent solution has a temperature that is about 1° C. to about 5° C. higher than the temperature of the melted petrolatum.

14. The method according to claim 1, wherein the petrolatum-based composition comprises from about 0.01% to about 5% by weight terbinafine HCl.

15. The method according to claim 1, wherein the petrolatum-based composition comprises from about 0.01% to about 5% by weight ciclopirox.

16. The method according to claim 1, wherein the petrolatum-based composition comprises from about 0.01% to about 5% by weight ciclopirox olamine.

17. The method according to claim 1, wherein the petrolatum-based composition comprises from about 0.01% to about 5% by weight clotrimazole.

18. The method according to claim 1, wherein the petrolatum-based composition comprises from about 0.01% to about 5% by weight miconazole (miconazole nitrate).

19. A method of treating a fungal infection of the nail in a subject, the method comprising applying a petrolatum-based composition to the nail of a subject in need of treatment, the composition comprising a pharmaceutically effective amount of terbinafine HCl in a petrolatum carrier,
wherein the terbinafine HCl is dissolved in a polar solvent to form an anti-fungal agent solution, the anti-fungal agent solution dispersed in the petrolatum to form a stable suspension, and
wherein the petrolatum-based composition comprises greater than about 90% by weight petrolatum.

* * * * *